United States Patent

Tsutsui et al.

(10) Patent No.: US 9,775,498 B2
(45) Date of Patent: Oct. 3, 2017

(54) ENDOSCOPE SYSTEM (71) Applicant: OLYMPUS CORPORATION, Tokyo (JP)

(72) Inventors: Keisuke Tsutsui, Kawaguchi (JP); Fumiyuki Okawa, Tama (JP); Hiroyuki Usami, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/379,750

(22) Filed: Dec. 15, 2016

(65) Prior Publication Data

US 2017/0095141 A1    Apr. 6, 2017

Related U.S. Application Data

(63) Continuation of application No. PCT/JP2015/076516, filed on Sep. 17, 2015.

(30) Foreign Application Priority Data

Mar. 26, 2015 (JP) ................. 2015-064540

(51) Int. Cl.
*H04N 9/47* (2006.01)
*A61B 1/00* (2006.01)
(Continued)

(52) U.S. Cl.
CPC ............ *A61B 1/04* (2013.01); *A61B 1/00009* (2013.01); *A61B 1/00045* (2013.01);
(Continued)

(58) Field of Classification Search
CPC .... H04N 17/002; A61B 1/04; A61B 1/00009; A61B 1/00114; A61B 1/00121; A61B 1/00045; G02B 23/2484
See application file for complete search history.

(56) References Cited

U.S. PATENT DOCUMENTS 8,313,425 B2 * 11/2012 Shidara .............. A61B 1/00057
600/109
2007/0035797 A1 * 2/2007 Kanai ................ G02B 21/0028
600/101
(Continued)

FOREIGN PATENT DOCUMENTS

EP    2 868 255 A1    5/2015
JP    7-171096    7/1995
(Continued)

OTHER PUBLICATIONS

International Search Report dated Dec. 15, 2015 received in International Application No. PCT/JP2015/076516, together with an English-language translation.

(Continued)

*Primary Examiner* — Tsion B Owens
(74) *Attorney, Agent, or Firm* — Scully, Scott, Murphy & Presser, P.C.

(57) ABSTRACT

An endoscope system includes a head portion, a connector portion and a CCU. The head portion includes a test signal generating portion configured to generate a first test pattern signal. The connector portion includes: a test signal generating portion configured to generate a second test pattern signal which is a same pattern signal as the first test pattern; a first comparison circuit configured to output a comparison result of comparing the first test pattern signal with the second test pattern signal; and a test signal generating portion configured to generate a third test pattern signal. The CCU includes: a test signal generating portion configured to generate a fourth test pattern signal which is a same pattern signal as the third test pattern; and a second comparison circuit configured to output a comparison result of comparing the third test pattern signal with the fourth test pattern signal.

4 Claims, 8 Drawing Sheets

(51) Int. Cl.
　　　A61B 1/04　　　(2006.01)
　　　G02B 23/24　　(2006.01)
　　　H04N 17/00　　(2006.01)
(52) U.S. Cl.
　　　CPC ...... *A61B 1/00114* (2013.01); *A61B 1/00121* (2013.01); *G02B 23/2484* (2013.01); *H04N 17/002* (2013.01)

(56) References Cited

U.S. PATENT DOCUMENTS

| | | | | |
|---|---|---|---|---|
| 2009/0244273 | A1* | 10/2009 | Usami | G01B 31/318519 348/76 |
| 2013/0012777 | A1* | 1/2013 | Baum | A61B 1/00013 600/110 |
| 2013/0235175 | A1* | 9/2013 | Kazama | H04N 7/18 348/65 |
| 2014/0320619 | A1* | 10/2014 | Nakamura | A61B 1/00036 348/65 |
| 2014/0340496 | A1 | 11/2014 | Okawa et al. | |

FOREIGN PATENT DOCUMENTS

| | | |
|---|---|---|
| JP | 2002-199291 A | 7/2002 |
| JP | 2005-296467 A | 10/2005 |
| JP | 2011-206185 A | 10/2011 |
| WO | 2014/002732 A1 | 1/2014 |

OTHER PUBLICATIONS

Japanese Notification of Reasons for Rejection dated Jun. 7, 2016 received in Japanese Application No. 2016-509179, together with an English-language translation.

\* cited by examiner

ENDOSCOPE SYSTEM

CROSS REFERENCE TO RELATED APPLICATION

This application is a continuation application of PCT/JP2015/076516 filed on Sep. 17, 2015 and claims benefit of Japanese Application No. 2015-064540 filed in Japan on Mar. 26, 2015, the entire contents of which are incorporated herein by this reference.

BACKGROUND OF THE INVENTION

1. Field of the Invention

The present invention relates to an endoscope system, and in particular to an endoscope system capable of performing a bit error rate test.

2. Description of the Related Art

Conventionally, an endoscope system provided with an endoscope and configured to perform observation and various treatments of an examined site by inserting the elongated endoscope into a body cavity or the like has been widely used. As such an endoscope system, for example, an endoscope system in which a head-separated camera apparatus (a camera head) including a solid-state image pickup device is fitted to an eyepiece portion of an endoscope is disclosed in Japanese Patent Application Laid-Open Publication No. 2002-199291.

The camera head internally includes the solid-state image pickup device, and is configured with a head portion to be connected to the eyepiece portion of the endoscope, an electric cable extending from the head portion and a connector portion provided on a proximal end portion of the electric cable, and attachably and detachably connected to a camera control unit or a video processor via the connector portion. An image pickup signal from the solid-state image pickup device included in the camera head is inputted to the camera control unit. Then, by performing predetermined image processing for the inputted image pickup signal and outputting the image pickup signal to a connected monitor, the camera control unit displays an endoscope image on the monitor.

Recently, camera heads for medical use have been evolved in a manner that drive frequency is speeded up, accompanying increase in the number of pixels of solid-state image pickup devices, that amount of video data to be outputted increases and that a speed rate of transmitting video to a camera control unit increases. On the other hand, the camera control unit performs image processing such as video signal enlargement/reduction processing and area cutting-out so as to adjust an image pickup signal from a camera head to performance of a connected monitor, and outputs the image pickup signal to the monitor.

SUMMARY OF THE INVENTION

An endoscope system of an aspect of the present invention is an endoscope system including a head-separated camera apparatus including a head portion including an image pickup device and a connector portion integrally connected to the head portion via a cable, and a signal processing apparatus attachable to and detachable from the head-separated camera apparatus via the connector portion, wherein the head portion includes: a first test pattern generating portion configured to generate a first test pattern signal; and a first transmitting portion configured to transmit the first test pattern signal generated by the first test pattern generating portion via the cable; the connector portion includes: a first receiving portion configured to receive the first test pattern signal transmitted from the first transmitting portion; a first detection circuit configured to detect a predetermined data pattern from the first test pattern signal received by the first receiving portion and output a first generation starting signal; a second test pattern generating portion configured to generate a second test pattern signal, which is a same pattern signal as the first test pattern, based on the first generation starting signal; a first comparison circuit configured to output a comparison result of comparing the first test pattern signal with the second test pattern signal; a third test pattern generating portion configured to generate a third test pattern signal; and a second transmitting portion configured to transmit the third test pattern signal generated by the third test pattern generating portion; and the signal processing apparatus includes: a second receiving portion configured to receive the third test pattern signal transmitted from the second transmitting portion; a second detection circuit configured to detect a predetermined data pattern from the third test pattern signal received by the second receiving portion and output a second generation starting signal; a fourth test pattern generating portion configured to generate a fourth test pattern signal, which is a same pattern signal as the third test pattern, based on the second generation starting signal; and a second comparison circuit configured to output a comparison result of comparing the third test pattern signal with the fourth test pattern signal. The connector portion includes a circuit configured to generate a control signal to instruct the head portion to transmit a test pattern signal. The head portion includes a selection circuit configured to switch a transmit signal between a video signal and the test pattern signal based on the control signal.

DETAILED DESCRIPTION OF THE PREFERRED EMBODIMENT(S)

Embodiments of the present invention will be described in detail below with reference to drawings.

First Embodiment

Figure 1:
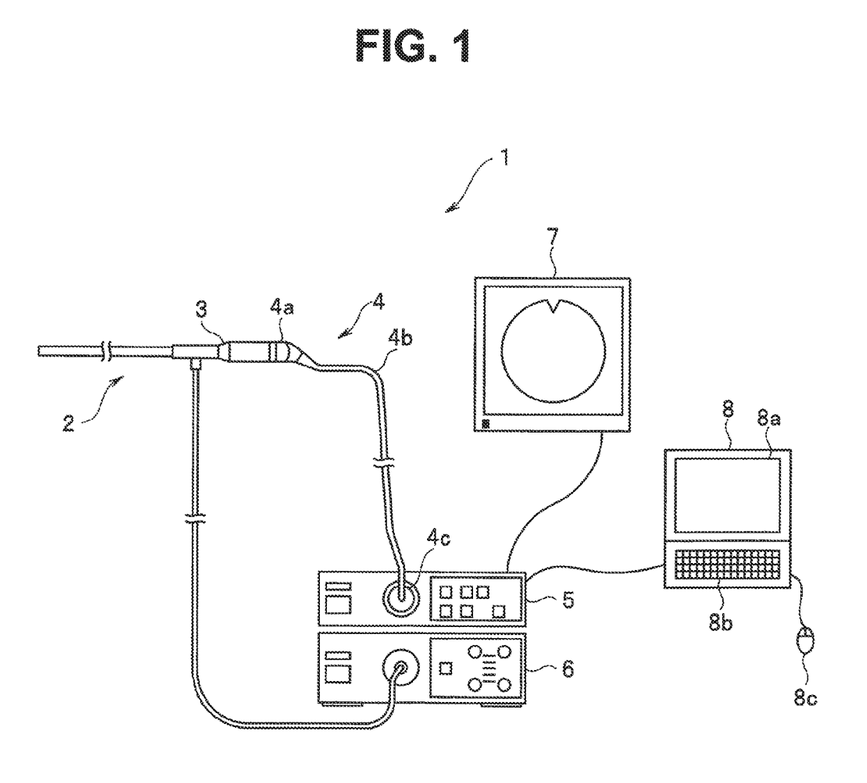
FIG. 1 is a diagram showing a configuration of an endoscope system according to a first embodiment.
Figure 2:
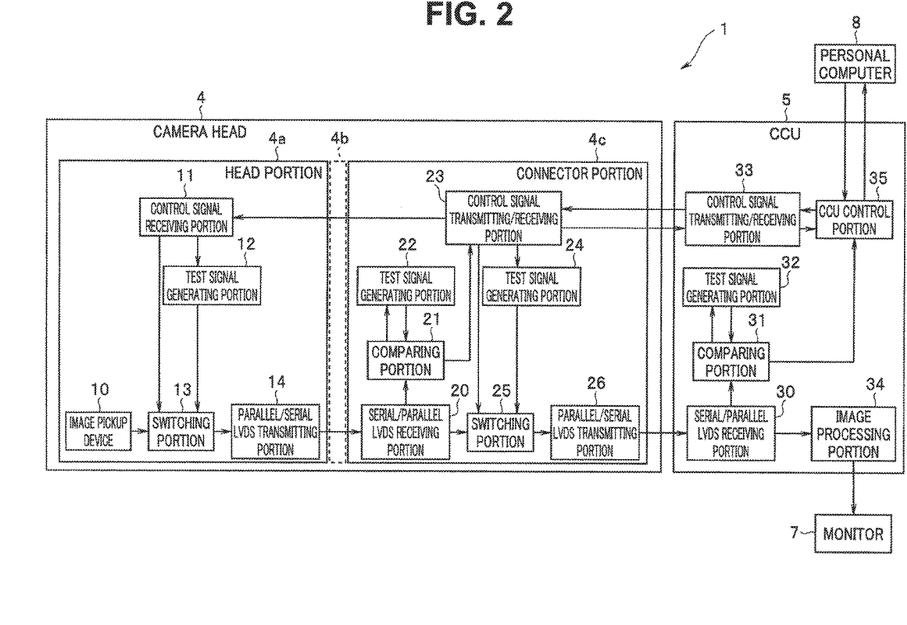
FIG. 2 is a diagram showing a detailed circuit configuration of a camera head and a camera control unit of the endoscope system according to the first embodiment.

FIG. 1 is a diagram showing a configuration of an endoscope system according to a first embodiment; and FIG. 2 is a diagram showing a detailed circuit configuration of a camera head and a camera control unit of the endoscope system according to the first embodiment.

As shown in FIG. 1, an endoscope system 1 is configured, for example, including an optical type endoscope 2, a camera head 4 attachably and detachably connected to an eyepiece portion 3 of the endoscope 2, a camera control unit (hereinafter referred to as the CCU) 5 to which the camera head 4 is attachably and detachably connected, a light source apparatus 6 configured to supply illuminating light to the endoscope 2, a monitor 7 configured to display an observation image by a video signal generated by an image processing portion of the CCU 5, which is to be described later, being inputted, and a personal computer 8 configured to give an instruction to start a comparison test to be described later, display a result of the comparison test, record the result of the comparison test, and so on.

The personal computer 8 includes a display portion 8a configured to display the result of the comparison test and the like; and a keyboard 8b and a mouse 8c for giving an instruction to start the comparison test, and the like. The personal computer 8 also includes a recording portion configured to record the result of the comparison test, which is not shown.

The camera head 4 as a head-separated camera apparatus includes a head portion 4a connected to the eyepiece portion 3, a cable 4b extending from the head portion 4a, and a connector portion 4c provided on a proximal end portion of the cable 4b. The camera head 4 is connected to the CCU 5 via the connector portion 4c.

Note that though description will be made on an assumption that the camera head 4 is connected to the endoscope 2, for example, other camera heads with different specifications of magnification ratio and the like can be connected to the endoscope 2. Further, operation instruments and the like, which are medical equipment, can be also connected to the CCU 5.

As shown in FIG. 2, the head portion 4a is configured including an image pickup device 10 configured with a CMOS sensor, a control signal receiving portion 11, a test signal generating portion 12, a switching portion 13, and a parallel/serial LVDS transmitting portion 14. Note that the image pickup device 10 is not limited to a CMOS sensor but may be a CCD sensor or the like.

Further, the connector portion 4c is configured including a serial/parallel LVDS receiving portion 20, a comparing portion 21, a test signal generating port on 22, a control signal transmitting/receiving portion 23, a test signal generating portion 24, a switching portion 25 and a parallel/serial LVDS transmitting portion 26.

Further, the CCU 5 is configured including a serial/parallel LVDS receiving portion 30, a comparing portion 31, a test signal generating portion 32, a control signal transmitting/receiving portion 33, an image processing portion 34 and a CCU control portion 35.

Illuminating light from the light source apparatus 6 is transmitted to the endoscope 2 via a light guide not shown and radiated to an object from a distal end face of an insertion portion via the light guide not shown in the insertion portion. Return light from the object is image-picked up by the image pickup device 10 of the head portion 4a. An image pickup signal obtained by the image pickup by the image pickup device 10 is outputted to the switching portion 13.

During normal endoscope observation, the switching portion 13 outputs the image pickup signal from the image pickup device 10 to the parallel/serial LVDS transmitting portion 14 of the connector portion 4c. Note that, when a comparison test to be described later is performed, the switching portion 13 outputs a test signal generated by the test signal generating portion 12 to the parallel/serial LVDS transmitting portion 14 based on a switching signal from the control signal receiving portion 11.

The parallel/serial LVDS transmitting portion 14 converts the inputted image pickup signal from parallel to serial and transmits the image pickup signal to the serial/parallel LVDS receiving portion 20 as an LVDS (low voltage differential signal). The serial/parallel LVDS receiving portion 20 converts the received image pickup signal from serial to parallel and outputs the image pickup signal to the switching portion 25.

During the normal endoscope observation, the switching portion 25 outputs the image pickup signal from the serial/parallel LVDS receiving portion 20 to the parallel/serial LVDS transmitting portion 26. Note that, when the comparison test to be described later is performed, the switching portion 25 outputs a test signal generated by the test signal generating portion 24 to the parallel/serial LVDS transmitting portion 26 based on a switching signal from the control signal transmitting/receiving portion 23.

The parallel/serial LVDS transmitting portion 26 converts the inputted image pickup signal from parallel to serial and transmits the image pickup signal to the serial/parallel LVDS receiving portion 30 as an LVDS. The serial/parallel LVDS receiving portion 30 converts the received image pickup signal from serial to parallel and outputs the image pickup signal to the image processing portion 34.

The image processing portion 34 performs predetermined image processing for the inputted image pickup signal to generate a video signal and outputs the generated video signal to the monitor 7 to display an observation image on the monitor 7.

Here, description will be made on an example of a procedure for a comparison test of data transmission between the head portion 4a and the connector portion 4c.

First, a user operates the keyboard 8b or the mouse 8c of the personal computer 8 to transmit a command giving an instruction to start a comparison test, from the personal computer 8 to the CCU control portion 35. The CCU control portion 35 transmits the command transmitted from the personal computer 8 to the control signal transmitting/receiving portion 33. The control signal transmitting/receiving portion 33 transmits the command transmitted from the CCU control portion 35 to the control signal transmitting/receiving portion 23 of the connector portion 4c, and the control signal transmitting/receiving portion 23 transmits the command transmitted from the control signal transmitting/receiving portion 33 to the control signal receiving portion 11 of the head portion 4a.

When receiving the command giving the instruction to start a comparison test, the control signal receiving portion 11 of the head portion 4a transmits a test signal generation starting signal to the test signal generating portion 12 and transmits a switching signal for switching to a test signal transmission mode to the switching portion 13. When the test signal generation starting signal is inputted, the test signal generating portion 12 as a first test pattern generating portion generates a test signal for performing a bit error rate test and outputs the test signal to the switching portion 13.

When the switching signal is inputted from the control signal receiving portion 11, the switching portion 13 outputs the test signal generated by the test signal generating portion 12 to the parallel/serial LVDS transmitting portion 14. The parallel/serial LVDS transmitting portion 14 as a first transmitting portion converts the test signal inputted from the switching portion 13 from parallel to serial and transmits the test signal as an LVDS to the serial/parallel LVDS receiving portion 20 of the connector portion 4c.

The serial/parallel LVDS receiving portion 20 as a first receiving portion receives the test signal from the parallel/serial LVDS transmitting portion 14, converts the test signal from serial to parallel and outputs the test signal to the comparing portion 21. When detecting a predetermined data pattern from the inputted test signal, the comparing portion 21 outputs a generation starting signal for starting generation of a test signal, to the test signal generating portion 22. When the generation starting signal is inputted, the test signal generating portion 22 as a second test pattern generating portion generates a test signal, which is a same pattern signal as the test signal generated by the test signal generating portion 12, and outputs the generated test signal to the comparing portion 21.

The comparing portion 21 compares the test signal from the serial/parallel LVDS receiving portion 20 and the test signal from the test signal generating portion 22, and outputs a comparison result to the control signal transmitting/receiving portion 23. If the comparison result indicates matching with each other, that is, if the test signal from the serial/parallel LVDS receiving portion 20 and the test signal from the test signal generating portion 22 match with each other, it is judged that there is not an error in the data transmission between the head portion 4a and the connector portion 4c. On the other hand, if the comparison result indicates not matching with each other, that is, if the test signal from the serial/parallel LVDS receiving portion 20 and the test signal from the test signal generating portion 22 do not match with each other, it is judged that there is an error in the data transmission between the head portion 4a and the connector portion 4c.

The control signal transmitting/receiving portion 23 transmits the comparison result from the comparing portion 21 to the control signal transmitting/receiving portion 33 of the CCU 5. The control signal transmitting/receiving portion 33 transmits the received comparison result to the CCU control portion 35. The personal computer 8 acquires the comparison result by accessing the CCU control portion 35, and displays the acquired comparison result on the display portion 8a or records the comparison result in the recording portion such as a memory.

Next, description will be made on an example of a procedure for a comparison test of data transmission between the connector portion 4c and the CCU 5.

First, the user operates the keyboard 8b or the mouse 8c of the personal computer 8 and transmits a command giving an instruction to start a comparison test, from the personal computer 8 to the CCU control portion 35. The CCU control portion 35 transmits the command transmitted from the personal computer 8 to the control signal transmitting/receiving portion 33, and the control signal transmitting/receiving portion 33 transmits the command transmitted from the CCU control portion 35 to the control signal transmitting/receiving portion 23 of the connector portion 4c.

When receiving the command giving the instruction to start a comparison test, the control signal transmitting/receiving portion 23 of the connector portion 4c transmits a test signal generation starting signal to the test signal generating portion 24 and transmits a switching signal for switching to the test signal transmission mode to the switching portion 25. When the test signal generation starting signal is inputted, the test signal generating portion 24 as a third test pattern generating portion generates a test signal for performing a bit error rate test and outputs the test signal to the switching portion 25.

When the switching signal is inputted from the control signal transmitting/receiving portion 23, the switching portion 25 outputs the test signal generated by the test signal generating portion 24 to the parallel/serial LVDS transmitting portion 26. The parallel/serial LVDS transmitting portion 26 as a second transmitting portion converts the test signal inputted from the switching portion 25 from parallel to serial and transmits the test signal as an LVDS to the serial/parallel LVDS receiving portion 30 of the CCU 5.

The serial/parallel LVDS receiving portion 30 as a second receiving portion receives the test signal from the parallel/serial LVDS transmitting portion 26, converts the test signal from serial to parallel and outputs the test signal to the comparing portion 31. When detecting a predetermined data pattern from the inputted test signal, the comparing portion 31 outputs a generation starting signal for starting generation of a test signal, to the test signal generating portion 32. When the generation starting signal is inputted, the test signal generating portion 32 as a fourth test pattern generating portion generates a test signal, which is a same pattern signal as the test signal generated by the test signal generating portion 24, and outputs the generated test signal to the comparing portion 31.

The comparing portion 31 compares the test signal from the serial/parallel LVDS receiving portion 30 and the test signal from the test signal generating portion 32 and outputs a comparison result to the CCU control portion 35. A judgment method is similar to the case of data transmission between the head portion 4a and the connector portion 4c. If the comparison result indicates matching with each other, it is judged that there is not an error in the data transmission between the connector portion 4c and the CCU 5. If the comparison result indicates not matching with each other, it is judged that there is an error in the data transmission between the connector portion 4c and the CCU 5.

The personal computer 8 acquires the comparison result by accessing the CCU control portion 35, and displays the acquired comparison result on the display portion 8a or stores the comparison result in a storage portion such as a memory.

Note that the command giving the instruction to perform a comparison test of data transmission between the head portion 4a and the connector portion 4c and the command giving the instruction to perform a comparison test of data transmission between the connector portion 4c and the CCU 5 may be a same command or may be different commands. That is, two comparison tests may be performed with one command, or a comparison test of data transmission between the head portion 4a and the connector portion 4c and a comparison test of data transmission between the connector portion 4c and the CCU 5 may be performed by a first command and a second command, respectively.

Here, a comparison test operation will be described with use of FIGS. 3 to 6.

Figure 3:
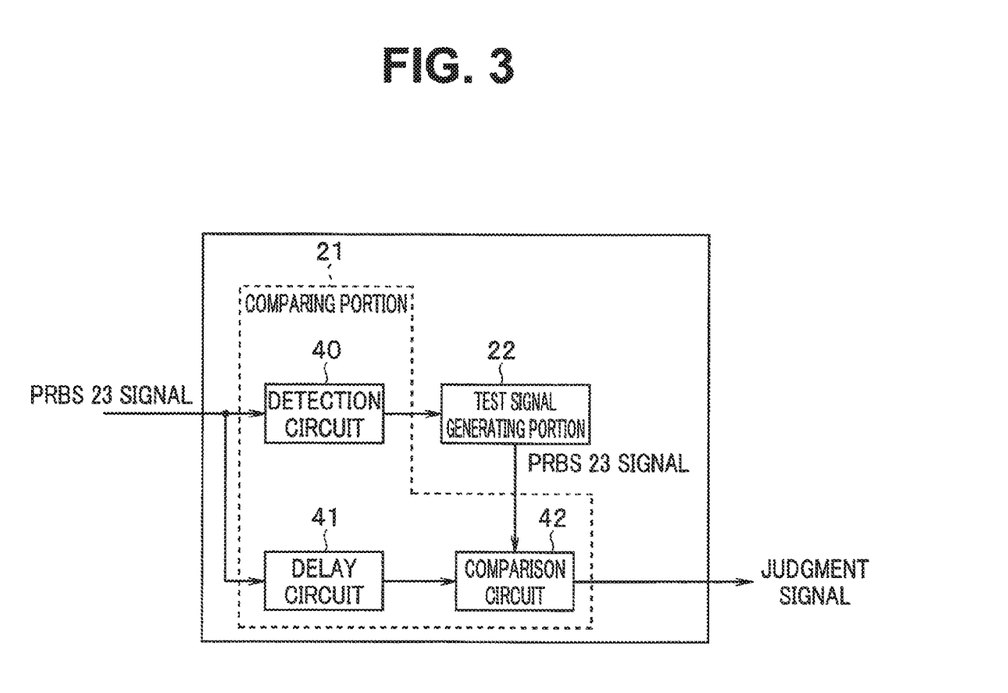
FIG. 3 is a diagram for illustrating a detailed circuit configuration of a comparing portion 21.
Figure 4:
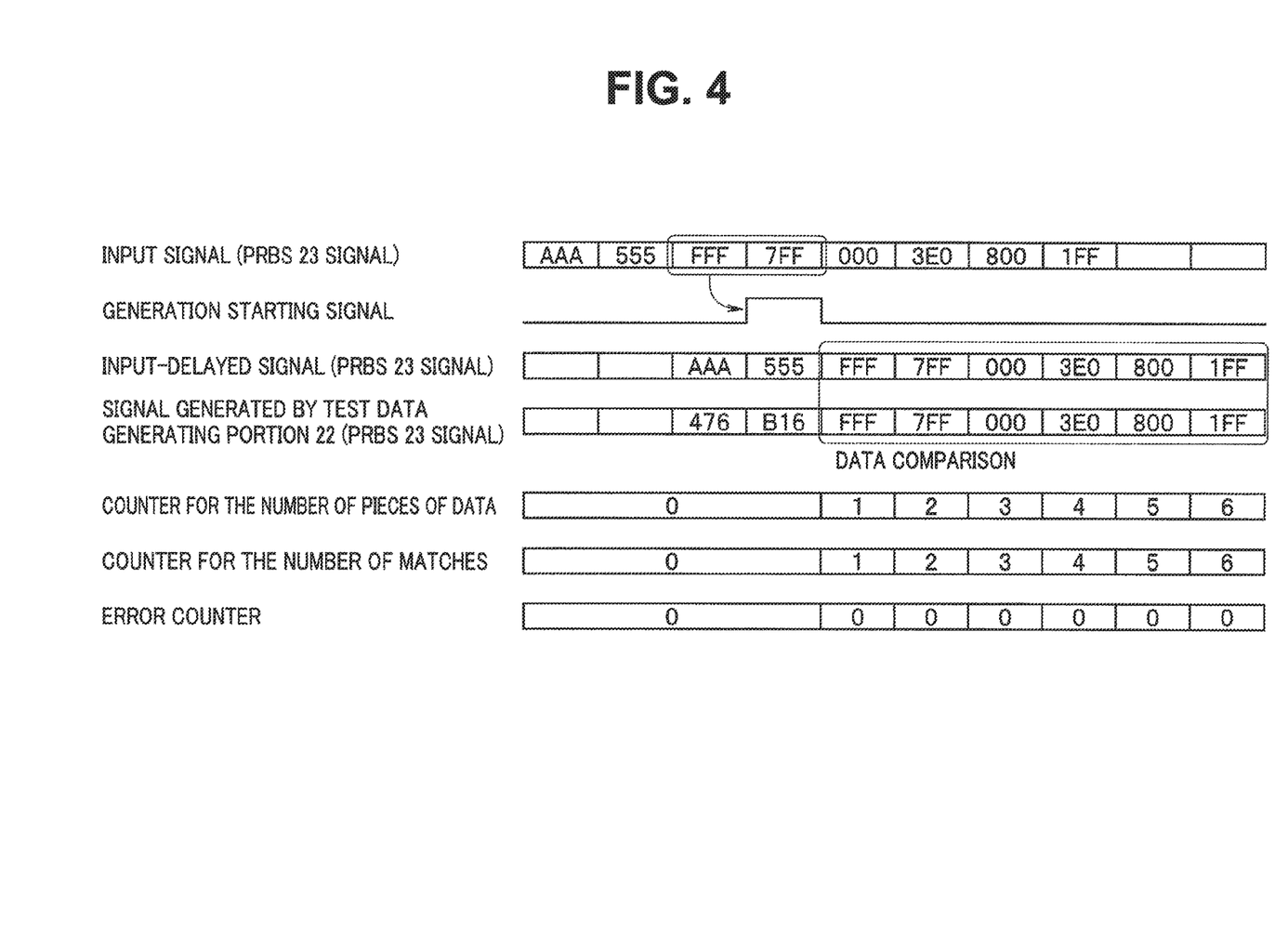
FIG. 4 is a diagram for illustrating an example of an operation of starting a comparison test in a comparison circuit.
Figure 5:
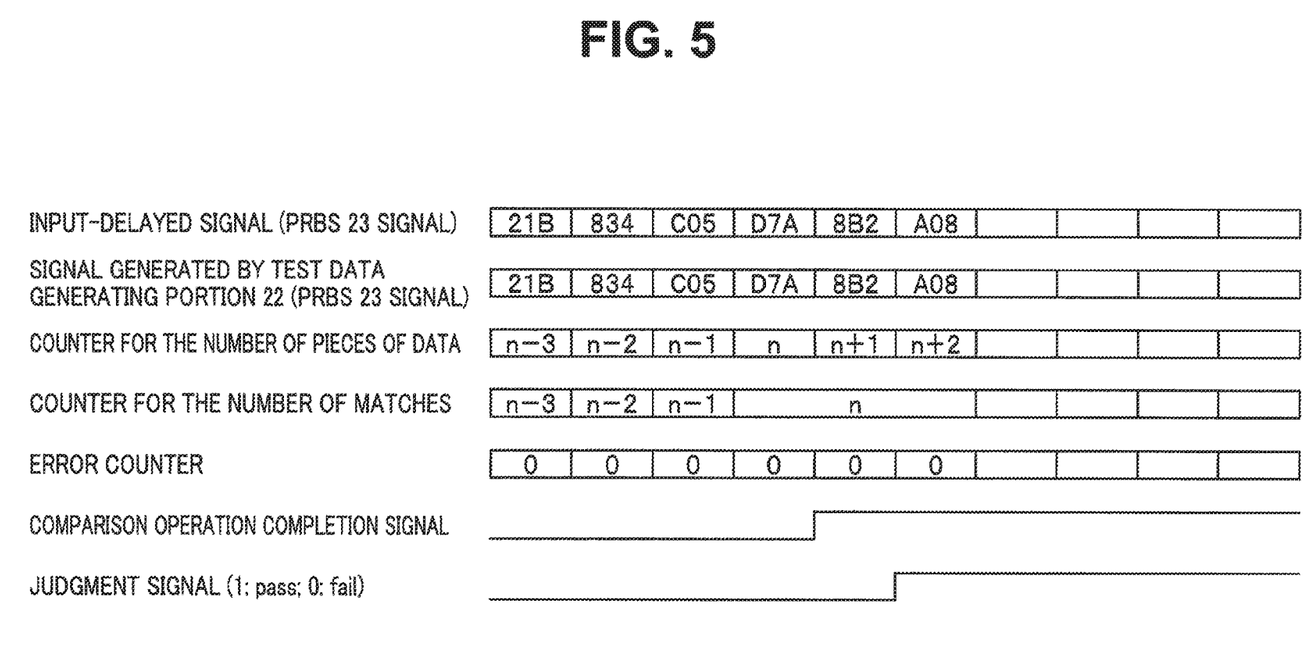
FIG. 5 is a diagram for illustrating an example of an operation of ending the comparison test in the comparison circuit when the test was passed.
Figure 6:
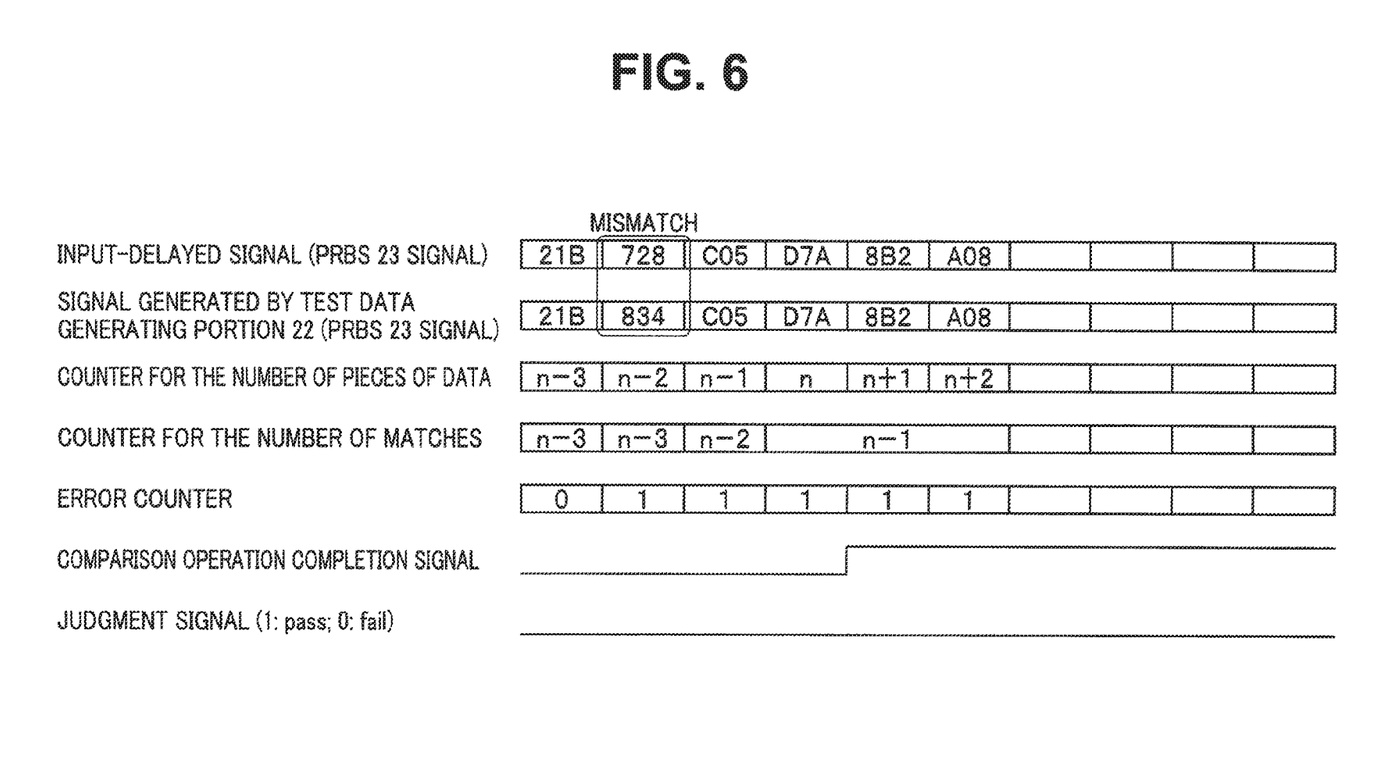
FIG. 6 is a diagram for illustrating an example of an operation of ending the comparison test in the comparison circuit when the test was failed.

FIG. 3 is a diagram for illustrating a detailed circuit configuration of the comparing portion 21; FIG. 4 is a diagram for illustrating an example of an operation of starting a comparison test in a comparison circuit; FIG. 5 is a diagram for illustrating an example of an operation of ending the comparison test in the comparison circuit when the test was passed; and FIG. 6 is a diagram for illustrating an example of an operation of ending the comparison test in the comparison circuit when the test was failed. Note that, since the comparing portion 21 and the comparing portion 31 have a same configuration and perform a same comparison test operation, the comparing portion 21 will be representatively described below.

As shown in FIG. 3, the comparing portion 21 is configured including a detection circuit 40, a delay circuit 41 and a comparison circuit 42. A PRBS (pseudo random bit sequence) 23 signal, which is used to evaluate a transmission quality of a high-speed digital signal, is generated by the test signal generating portion 12 of the head portion 4a as a test signal, and the generated PRBS 23 signal is inputted to the detection circuit 40 and the delay circuit 41 of the comparing portion 21 via the switching portion 13, the parallel/serial LVDS transmitting portion 14 and the serial/parallel LVDS receiving portion 20.

When detecting a predetermined data pattern from the inputted PRBS 23 signal, the detection circuit 40 transmits a generation starting signal (a trigger signal) for starting generation of a test signal, to the test signal generating portion 22. In an example of FIG. 4, the detection circuit 40 detects a data pattern of consecutive "FFF" and "7FF" from an inputted PRBS 23 signal and generates a generation starting signal.

When the generation starting signal is inputted from the detection circuit 40 of the comparing portion 21, the test signal generating portion 22 generates a data pattern (a PRBS 23 signal) in same order as the PRBS 23 signal inputted to the comparing portion 21 and outputs the generated PRBS 23 signal to the comparison circuit 42.

Further, the delay circuit 41 delays the inputted PRBS 23 signal by a predetermined period, for example, by two clocks, and outputs the PRBS 23 signal delayed by two clocks, to the comparison circuit 42.

As shown in FIG. 4, after the generation starting signal is generated by the detection circuit 40, the comparison circuit 42 compares the PRBS 23 signal generated by the test signal generating portion 22 and the PRBS 23 signal inputted from the delay circuit 41 and confirms whether the signals match with each other in a predetermined amount of data.

The comparison circuit 42 is provided with a counter configured to count the number of pieces of data compared, a counter configured to count the number of matches among the pieces of data compared, and an error counter configured to count the number of errors by subtracting the number of matches from the number of pieces of data compared.

The comparison circuit 42 detects whether the number of errors of the error counter is 0 or not and outputs a detection result as a judgment signal (a comparison result) shown by 0 (low) or 1 (high). For example, the comparison circuit 42 outputs a judgment signal of 1 (high) indicating that the test was passed if the number of errors is 0, and outputs a judgment signal of 0 (low) indicating that the test was failed if the number of errors is 1 or larger.

Note that, though the comparison circuit 42 judges whether a test was passed or failed based on whether the number of errors is 0 or not, the judgment is not limited to that, and a predetermined threshold may be used to perform the judgment. More specifically, for example, the comparison circuit 42 judges that a test was passed if the number of errors of the error counter is below a predetermined number of errors (a predetermined threshold), and judges that the test was failed if the number of errors of the error counter is the predetermined number of errors (the predetermined threshold) or larger.

As shown in FIG. 5, when comparison of n pieces of data is performed, a comparison operation completion signal is inputted to the comparison circuit 42 after the comparison of the n pieces of data is executed. Note that, when the counter configured to count the number of pieces of data reaches n, the comparison operation completion signal is outputted from the counter. When the comparison operation completion signal is inputted, the comparison circuit 42 confirms the number of errors of the error counter. In the example shown in FIG. 5, since the number of errors of the error counter is 0, the comparison circuit 42 outputs a judgment signal of 1 (high) indicating that the test was passed. On the other hand, in an example shown in FIG. 6, since the number of errors of the error counter is 1, the comparison circuit 42 outputs a judgment signal of 0 (low) indicating that the test was failed.

As described above, the endoscope system 1 is adapted so that a bit error rate test between the head portion 4a and the connector portion 4c of the camera head 4 is performed by the comparing portion 21, and a bit error rate test between the connector portion 4c and the CCU 5 is performed by the comparing portion 31. Thereby, the endoscope system 1 judges whether or not a transmission error has occurred between the head portion 4a and the connector portion 4c and whether or not a transmission error has occurred between the connector portion 4c and the CCU 5.

Therefore, according to the endoscope system of the present embodiment, it is possible to, when a transmission error has occurred, certainly identify a position where the error has occurred.

Further, since the endoscope system 1 can perform a bit error rate test between the bead portion 4a and the connector portion 4c and between the connector portion 4c and the CCU 5, it is possible to, when a transmission error occurs at time of transmitting an image pickup signal, certainly identify a position where the error has occurred.

Note that, though the embodiment has been described with use of an example in which a bit error rate test is executed from the personal computer 8, such a configuration may be adopted that specifications of a bit error rate test are introduced into the CCU 5 to make it possible to select the bit error rate test from a menu of the CCU 5, execute the test, and display and record a result.

Second Embodiment

Next, a second embodiment will be described.

Figure 7:
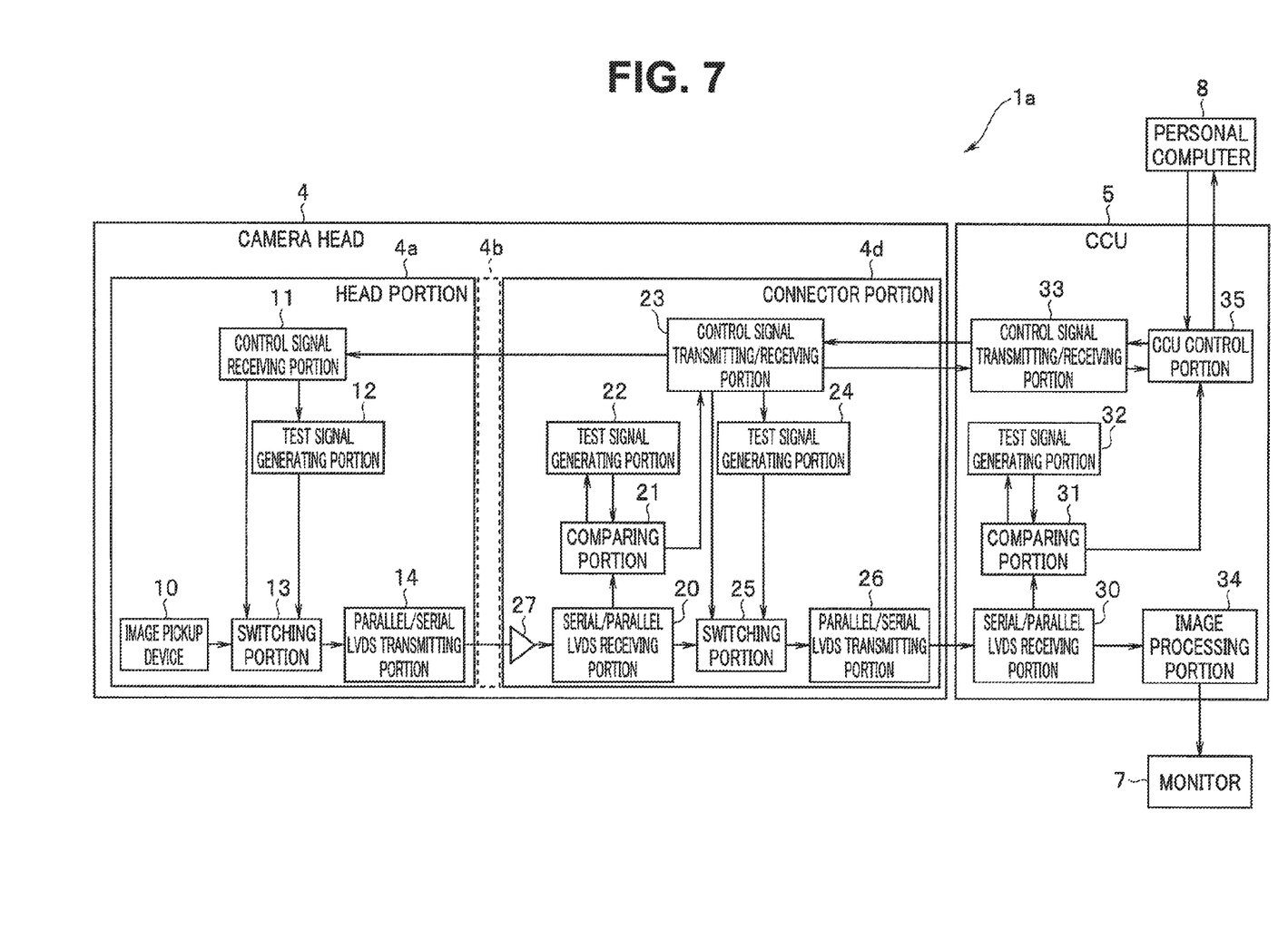
FIG. 7 is a diagram showing a detailed circuit configuration of a camera head and a camera control unit of an endoscope system according to a second embodiment.

FIG. 7 is a diagram showing a detailed circuit configuration of a camera head and a camera control unit of an endoscope system according to the second embodiment. Note that, in FIG. 7, components similar to those of FIG. 2 are given same reference numerals, and description of the components will be omitted.

As shown in FIG. 7, an endoscope system 1a of the present embodiment is configured with use of a connector portion 4d instead of the connector portion 4c of FIG. 2. The connector portion 4d is configured including an amplifier 27 at a previous stage of the serial/parallel LVDS receiving portion 20.

Generally, since the cable 4b has a length of several meters, a signal transmitted from the parallel/serial LVDS transmitting portion 14 deteriorates while being transmitted through the cable 4b. The amplifier 27 amplifies the signal which has deteriorated while being transmitted through the cable 4b to output the signal to the serial/parallel LVDS receiving portion 20.

Note that, though the configuration in which the connector portion 4d includes the amplifier 27 is adopted, the configuration is not limited to that, and, for example, a configuration is also possible in which the head portion 4a includes the amplifier 27. More specifically, the amplifier 27 is provided on a subsequent stage of the parallel/serial LVDS transmitting portion 14 on that a signal transmitted from the parallel/serial LVDS transmitting portion 14 is amplified and then transmitted through the cable 4b. Other components and operations are similar to those of the first embodiment.

Figure 8:
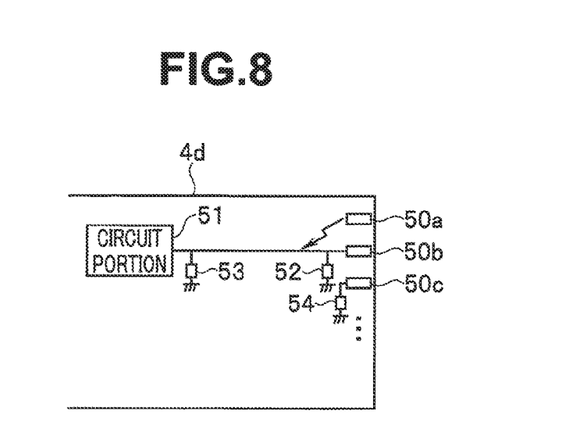
FIG. 8 is a diagram for illustrating a configuration of a connector portion 4d.

Here, a configuration of the connector portion 4d will be described. FIG. 8 is a diagram for illustrating the configuration of the connector portion 4d.

As shown in FIG. 8, the connector portion 4d includes a plurality of connection pins 50a, 50b, 50c, . . . for electrically connecting to the CCU 5. There may be a case where ESD (electrostatic discharge) is applied to the plurality of connection pins 50a, 50b, 50c, and an ESD protection member for protecting internal circuits, an IC, and the like from the ESD is provided.

As shown in FIG. 8, since the connection pin 50b is connected to a circuit portion 51, an ESD protection member 52 configured with an ESD protection diode, varistor or the like is provided immediately near the connection pin 50b in order to protect the circuit portion 51 from ESD.

Recently, with increase in speed of digital transmission, capacity of the ESD protection member 52 has been reduced. Therefore, when a large ESD is applied to the connection pin 50b, there is a possibility that the circuit portion 51 cannot be protected. Further, there may be a case where ESD applied to the connection pin 50a unused conies to a connection line connecting the connection pin 50b and circuit portion 51.

Therefore, in the present embodiment, an ESD protection member 53 is provided immediately near the circuit portion 51 also so that the circuit portion 51 can be protected even if a large ESD is applied to the connection pin 50b or even if ESD applied to the unused connection pin 50a conies to the connection line. Further, in order to prevent the ESD applied to the unused connection pin 50a from coming to the connection line, for example, an ESD protection member 54 is provided for the unused connection pin 50c also. Note that an ESD protection member may be provided for the unused connection pin 50a also similarly to the connection pin 50c though it is not shown.

Figure 9A:
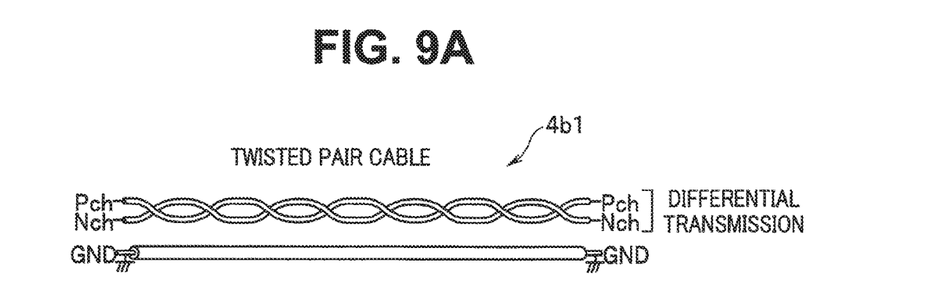
FIG. 9A is a diagram for illustrating a configuration of a twisted pair cable.
Figure 9B:
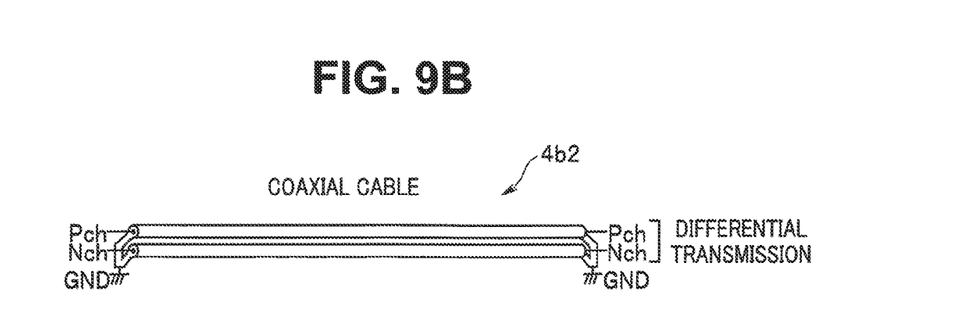
FIG. 9B is a diagram for illustrating a configuration of a coaxial cable.

Next, a configuration of the cable 4b of the camera head 4 of the present embodiment will be described. FIG. 9A is a diagram for illustrating a configuration of a twisted pair cable; and FIG. 9B is a diagram for illustrating a configuration of a coaxial cable.

Generally, in a case of transmitting a digital differential signal such as an LVDS through the cable 4b, a twisted pair cable 4b1 obtained by twisting two single wires to make a pair is used as shown in FIG. 9A. As for the twisted pair cable 4b1, a Pch and an Nch are connected to one and the other of the pair elements, respectively, and differential impedance between the pair elements is designed to be 100Ω. Further, the twisted pair cable 4b1 requires a single GND wire in addition to the two Pch and Nch wires.

An image pickup signal from the head portion 4a is transmitted to the connector portion 4d and the CCU 5 by a digital differential signal. However, increase in speed of transmission rate has been remarkable recently because of increase in the number of pixels of and the number of plates of the image pickup device 10, and a technical hurdle of transmission becomes higher. In order to cope with high-speed transmission, it is a conventional technique to increase a thickness of a cable itself or to divide data to be transmitted and increase the number of lanes so as to decrease a transmission rate per lane.

However, the twisted pair cable 4b1 is twisted, and, therefore, if a twist pitch is wide, a distance between the pair elements changes when the twisted pair cable 4b1 bends, and the differential impedance cannot be maintained. On the other hand, if the twist pitch of the twisted pair cable 4b1 is narrow, the distance between the pair elements does not change, but the twisted pair cable 4b1 itself becomes hard, and it becomes difficult to lay the twisted pair cable 4b1.

Further, when the number of lanes is increased to increase the number of pairs, the number of twisted pair cables 4b1 increases for that, and an integrated cable diameter becomes large. When the integrated cable diameter becomes large, an integrated cable becomes hard, and it becomes difficult to lay the integrated cable. Since great importance is also attached to how easy the cable 4b can be laid in medical sites, difficulty in laying the cable 4b leads to a demerit for users. Therefore, in the camera head 4 in which the cable 4b is not fixed but bent or moved, there is a possibility that the twisted pair cable 4b1 cannot demonstrate sufficient performance.

Therefore, in the present embodiment, coaxial cables 4b2 shown in FIG. 9B are used for the cable 4b instead of the twisted pair cable 4b1 of FIG. 9A to perform differential transmission. That is, digital differential transmission of the camera head 4 is performed by the two coaxial cables 4b2 instead of the twisted pair cable 4b1. A single characteristic impedance of the coaxial cables 4b2 is not disturbed even if the coaxial cables 4b2 are bent. Further, since each of the coaxial cables 4b2 is shielded, disturbance resistance is higher than that of the twisted pair cable 4b1.

Further, in the case of increasing the number of lanes because of necessity of high-speed transmission, it is possible to secure GND by shields of the coaxial cables 4b2, by using the coaxial cables 4b2, Therefore, it is possible to delete the single GND wire of the twisted pair cable 4b1. As a result, even if the number of lanes is increased, the total diameter of the cable 4b is influenced little, and it is possible to easily lay the cable 4b.

Thus, by using the coaxial cables 4b2 at the time of transmitting a differential digital signal by divided differential signals of multiple lanes, it is possible to delete the single GND wire of the twisted pair cable 4b1 and realize high-speed transmission and diameter reduction of the cable 4b at the same time.

In a configuration like a multi-lane transmission configuration, it is possible to identify an error of each individual transmission lane by executing a bit error rate test for each transmission lane.

The present invention is not limited to the embodiments described above, and various modifications, alterations and the like are possible within a range not changing the spirit of the present invention.

What is claimed is:

1. An endoscope system comprising a head-separated camera apparatus including a head portion including an image pickup device and a connector portion integrally connected to the head portion via a cable, and a signal processing apparatus attachable to and detachable from the head-separated camera apparatus via the connector portion, wherein
the head portion comprises:

a first test pattern generating portion configured to generate a first test pattern signal; and a first transmitting portion configured to transmit the first test pattern signal generated by the first test pattern generating portion via the cable;

the connector portion comprises:

a first receiving portion configured to receive the first test pattern signal transmitted from the first transmitting portion;

a first detection circuit configured to detect a predetermined data pattern from the first test pattern signal received by the first receiving portion and output a first generation starting signal;

a second test pattern generating portion configured to generate a second test pattern signal, which is a same pattern signal as the first test pattern, based on the first generation starting signal;

a first comparison circuit configured to output a comparison result of comparing the first test pattern signal with the second test pattern signal;

a third test pattern generating portion configured to generate a third test pattern signal; and a second transmitting portion configured to transmit the third test pattern signal generated by the third test pattern generating portion; and the signal processing apparatus comprises:

a second receiving portion configured to receive the third test pattern signal transmitted from the second transmitting portion;

a second detection circuit configured to detect a predetermined data pattern from the third test pattern signal received by the second receiving portion and output a second generation starting signal;

a fourth test pattern generating portion configured to generate a fourth test pattern signal, which is a same pattern signal as the third test pattern, based on the second generation starting signal; and a second comparison circuit configured to output a comparison result of comparing the third test pattern signal with the fourth test pattern signal.

2. The endoscope system according to claim 1, wherein the head portion comprises a first switching portion configured to switch between the image pickup signal and the first test pattern signal to output the image pickup signal or the first test pattern signal to the first transmitting portion;

the connector portion comprises a second switching portion configured to switch between the image pickup signal and the third test pattern signal to output the image pickup signal or the third test pattern signal to the second transmitting portion;

the first transmitting portion transmits the image pickup signal or the first test pattern signal to the first receiving portion via the cable; and the second transmitting portion transmits the image pickup signal or the third test pattern signal to the second receiving portion.

3. The endoscope system according to claim 2, wherein the first transmitting portion converts the image pickup signal or the first test pattern signal to differential serial data and outputs the differential serial data via the cable; and the cable is a pair of two coaxial cables for transmitting the differential serial data.

4. The endoscope system according to claim 1, wherein the first test pattern signal is a test signal for a bit error rate test.

* * * * *